United States Patent [19]

Benedikter et al.

[11] 4,421,755
[45] Dec. 20, 1983

[54] METHOD OF TREATING CORONARY HEART DISEASE WITH IMIDAZO(4,5-B)PYRIDINES

[75] Inventors: Lothar Benedikter; Eberhard Kutter, both of Biberach, Fed. Rep. of Germany

[73] Assignee: Dr. Karl Thomae Gesellschaft mit beschränkter Haftung, Biberach an der Riss, Fed. Rep. of Germany

[21] Appl. No.: 349,838

[22] Filed: Feb. 18, 1982

[30] Foreign Application Priority Data

Mar. 3, 1981 [DE]  Fed. Rep. of Germany ....... 3108027

[51] Int. Cl.³ .................... A61K 31/435; A61K 31/44
[52] U.S. Cl. ..................................... 424/256; 424/263
[58] Field of Search ................. 424/256, 263; 546/118

[56] References Cited

U.S. PATENT DOCUMENTS 3,985,891  10/1976  Kutter et al. ......................... 424/263

Primary Examiner—Jerome D. Goldberg
Assistant Examiner—John W. Rollins, Jr.
Attorney, Agent, or Firm—Hammond & Littell, Weissenberger & Muserlian

[57] ABSTRACT

Pharmaceutical compositions containing, as an active ingredient, a compound of the formula

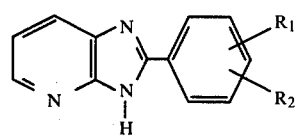

wherein $R_1$ is alkoxy of 1 to 4 carbon atoms, and
$R_2$ is (alkyl of 1 to 4 carbon atoms) sulfinyl, or a non-toxic, pharmacologically acceptable acid addition salt thereof; and a method of using the same for the treatment of coronary heart diseases or coronary spasms.

3 Claims, No Drawings

METHOD OF TREATING CORONARY HEART DISEASE WITH IMIDAZO(4,5-B)PYRIDINES

This invention relates to a novel method of treating coronary heart disease with known imidazo[4,5-b]pyridines.

THE PRIOR ART

German Pat. No. 2,305,339 and U.S. Pat. No. 3,985,891 disclose, inter alia, certain imidazo[4,5-b]pyridines of the formula

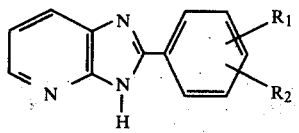

wherein $R_1$ is alkoxy of 1 to 4 carbon atoms, and $R_2$ is (alkyl of 1 to 4 carbon atoms)sulfinyl, and non-toxic, pharmacologically acceptable acid addition salts thereof. The compounds and their salts are disclosed to be useful as cardiotonics, anticoagulants and for altering the blood pressure.

THE INVENTION

We have discovered that the compounds embraced by formula I above and their non-toxic, pharmacologically acceptable acid addition salts also exhibit coronary dilating and peripheral vasodilating activities in warm-blooded animals such as dogs, which correspond to those of organic nitro-compounds such as nitroglycerin, and are therefore useful for the treatment of coronary diseases of the heart.

Specific examples of suitable substituents $R_1$ and $R_2$ in formula I are the following:

$R_1$: Methoxy, ethoxy, propoxy, isopropoxy and butoxy.

$R_2$: Methylsulfinyl, ethylsulfinyl, propylsulfinyl, isopropylsulfinyl and isobutylsulfinyl.

Preferred compounds are those where $R_1$ is in the 2-position and $R_2$ is in the 4-position of the phenyl ring, and especially those where $R_1$ is methoxy and $R_2$ is methylsulfinyl.

Particularly preferred is 2-(2-methoxy-4-methylsulfinyl-phenyl)-1H-imidazo[4,5-b]pyridine or a non-toxic, pharmacologically acceptable acid addition salt thereof.

The novel properties of the compounds of the formula I and their non-toxic, pharmacologically acceptable acid addition salts were ascertained by the test methods described below, and Tables I and II show the results of these tests for 2-(2-methoxy-4-methylsulfinyl-phenyl)-1H-imidazo[4,5-b]pyridine.

1. Effect on peripheral resistance and venous capacity in anesthetized dogs

Male and female dogs weighing 10 to 22 kg were anesthetized with pentobarbital-Na (30 mg/kg i.v.). Blood clotting was prevented by intravenous injection of heparin (1000 U/kg). The central venous pressure was measured with a Statham pressure transducer (P 23 Db), using a polyethylene catheter in the vena cava. The arterial blood pressure was measured with another Statham pressure transducer, using a catheter in the aorta abdominalis. The cardiac output was measured with the HZV apparatus made by the Fischer Company (BN 7206), using the cold dilution method. Cold saline solution was injected into the right auricle, and the temperature changes in the arch of the aorta were measured with an NTC-thermistor. The difference between the arterial blood pressure and central venous pressure was divided by the cardiac output, and in this way the peripheral resistance was obtained.

Changes in the venous capacity were measured, using the method of SUGA et al. [Pflügers Arch. 361, 95–98 (1975)]. For this purpose, the central venous pressure was kept constant by means of an overflow vessel and a catheter opening into the vena cava. Any changes in volume in the overflow vessel, which are identical to changes in venous capacity, were recorded. The test compound was dissolved in physiological saline solution and injected via a vena saphena.

The following results were obtained:

TABLE I

| Dose mg/kg i.v. | n | Changes in peripheral resistance % | Changes in venous capacity ml/kg |
|---|---|---|---|
| 0.5 | 5 | −10 | +2.0 |
| 1.0 | 7 | −14 | +2.9 |
| 2.5 | 6 | −21 | +5.3 |
| 5.0 | 4 | −32 | +9.7 | n = number of dogs

All effects were significant ($P < 0.05$)

2. Effect on coronary blood flow in anesthetized dogs 11 dogs of both sexes, weighing 21 to 26 kg, were anesthetized by intravenous administration of an anesthetic mixture (given in mg/kg) of α-chloralose (54), urethane (270) and pentobarbital (10). After tracheotomy, the animals were artificially ventilated. The thorax was opened on the left, in the fifth intercostal space, the heart rate was exposed and, in order to measure coronary blood flow, extracorporeal circulation was set up between the left arteria carotis and the arteria coronaria descendens of the left ventricle. The measuring head of an electromagnetic blood-flow measuring apparatus (Biotronex BL-610) was incorporated into the circulation. The test compound was dissolved in physiological saline solution and injected into a vena saphena.

The following changes in coronary blood flow were observed (n=11):

TABLE II

| Dose mg/kg i.v. | Increase in coronary blood flow % |
|---|---|
| 0.1 | +2.2 |
| 0.25 | +6.5 |
| 0.5 | +11.6 |
| 1.0 | +15.8 |

All effects were significant ($p < 0.05$).

In view of their newly discovered biological properties, the compounds of the formula I and the physiologically acceptable acid addition salts thereof with inorganic or organic acids are also suitable for the treatment of coronary heart disease such as angina pectoris, coronary insufficiency and cardiac infarct, or for the prophylaxis of coronary spasms such as may occur, for example, in coronarography.

For pharmaceutical purposes the compounds of the formula I or their non-toxic, pharmacologically acceptable acid addition salts are administered to warm-blooded animals perorally, parenterally or rectally as active ingredients in customary pharmaceutical compositions, that is, compositions consisting essentially of an inert pharmaceutical carrier and effective amount of the active ingredient, such as tablets, coated pills, capsules, wafers, powders, solutions, suspensions, emulsions, syrups, suppositories and the like. An effective amount of the compounds used in the method of the present invention is from 0.71 to 7.14 mgm/kg body weight, preferably 1.42 to 3.57 mgm/kg body weight, administered 2 to 4 times daily.

The following examples illustrate a few pharmaceutical compositions comprising a compound of the formula I or a non-toxic, pharmacologically acceptable acid addition salt thereof as an active ingredient and represent the best modes contemplated of using the invention. The parts are parts by weight unless otherwise specified.

EXAMPLE 1

Suppositories

The suppository composition is compounded from the following ingredients:

| | |
|---|---|
| 2-(2-Methoxy-4-methylsulfinyl-phenyl)-1H—imidazo[4,5-b]pyridine | 200 parts |
| Suppository base (e.g. cocoa butter) | 1,500 parts |
| Total | 1,700 parts |

Preparation

The suppository base is melted and cooled to 38° C., the milled active ingredient is homogeneously dispersed therein, the composition is cooled to 35° C., and 1700 mgm-portions thereof are poured into cooled suppository molds and allowed to harden therein. Each suppository is a rectal dosage unit composition containing 200 mgm of the active ingredient.

EXAMPLE 2

Capsules

The capsule filler composition is compounded from the following ingredients:

| | |
|---|---|
| 2-(2-Methoxy-4-methylsulfinyl-phenyl)-1H—imidazo[4,5-b]-pyridine hydrochloride | 100.0 parts |
| Corn starch | 56.0 parts |
| Lactose, powdered | 42.6 parts |
| Magnesium stearate | 1.4 parts |
| Total | 200.0 parts |

Preparation

A mixture of the active ingredient, corn starch and lactose is uniformly moistened with a mixture of ethanol and water, the moist mass is forced through a 1.5 mm-mesh screen, and the resulting granulate is dried. The dry granulate is admixed with the magnesium stearate, and 200 mgm-portions of the composition are filled into No. 2 hard gelatin capsules. Each capsule is an oral dosage unit composition containing 100 mgm of the active ingredient.

EXAMPLE 3

Infusion solution

The solution is compounded from the following ingredients:

| | |
|---|---|
| 2-(2-Methoxy-4-methylsulfinyl-phenyl)-1H—imidazo[4,5-b]-pyridine | 1.0 parts |
| Sodium chloride | 4,445 parts |
| 1N hydrochloric acid | 2.4 parts |
| Water for injection q.s. ad | 500.0 parts |

Preparation

The sodium chloride, the hydrochloric acid and the active ingredient are successively dissolved in the water for injection. The resulting pH 2.7 solution is filtered, and the filtrate is filled into 500 ml-infusion bottles which are subsequently sterilized for 20 minutes at 121° C. in superheated steam. Each bottle contains 1 gm of the active ingredient.

EXAMPLE 4

Tablets

The tablet composition is compounded from the following ingredients:

| | |
|---|---|
| 2-(2-Methoxy-4-methylsulfinyl-phenyl)-1H—imidazo[4,5-b]-pyridine | 200 parts |
| Corn starch | 60 parts |
| Lactose | 127 parts |
| Gelatin | 10 parts |
| Magnesium stearate | 3 parts |
| Total | 400 parts |

Preparation

The active ingredient, the corn starch and the lactose are intimately admixed with each other, the mixture is granulated with an aqueous solution of the gelatin, the granulate is dried, screened and admixed with the magnesium stearate, and the composition is compressed into 400 mgm-tablets. Each tablet is an oral dosage unit composition containing 200 mgm of the active ingredient.

EXAMPLE 5

Delayed-release tablets

The tablet composition is compounded from the following ingredients:

| | |
|---|---|
| 2-(2-Methoxy-4-methylsulfinyl-phenyl)-1H—imidazo[4,5-b]-pyridine | 250.0 parts |
| Polyacrylic acid | 210.0 parts |
| Polyvinylpyrrolidone | 22.5 parts |
| Lactose | 10.0 parts |
| Magnesium stearate | 7.5 parts |
| Total | 500.0 parts |

Preparation

The active ingredient, the polyacrylic acid, the lactose and the polyvinylpyrrolidone are mixed together in a suitable mixer and moistened with water. After moist granulation through a 1.6 mm-mesh screen, the granules are dried at about 45° C. and again passed through a 1.0 mm-mesh screen. After the addition of the magnesium stearate, the composition is compressed into 500 mgm tablets. Each tablet is an oral dosage unit composition containing 250 mgm of the active ingredient.

Release in vitro: (USP-XX model, 100 rpm, USP-gastric juice, 37° C.)
1 hour 27% of active ingredient
2 hours 42 of active ingredient
3 hours 55% of active ingredient
4 hours 66% of active ingredient
5 hours 76% of active ingredient
6 hours 84% of active ingredient
7 hours 91% of active ingredient Any one of the other compounds embraced by formula I or a non-toxic, pharmacologically acceptable acid addition salt thereof may be substituted for the particular active ingredient in Examples 1 through 5. Likewise, the amount of active ingredient in these illustrative examples may be varied to achieve the effective dosage range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of treating angina pectoris, coronary insufficiency or cardiac infarct in a warm-blooded animal in need thereof which comprises perorally, parenterally or rectally administering to said animal an effective coronary dilating and peripheral vasodilating amount of a compound of the formula

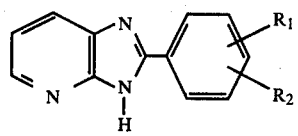

wherein $R_1$ is alkoxy of 1 to 4 carbon atoms, and
$R_2$ is (alkyl of 1 to 4 carbon atoms) sulfinyl, or non-toxic, pharmacologically acceptable acid addition salt thereof.

2. The method of claim 1, wherein $R_1$ is in the 2-position and $R_2$ is in the 4-position of the phenyl ring.

3. The method of claim 1, where said compound is 2-(2-methoxy-4-methylsulfinyl-phenyl)-1H-imidazo[4,5-b]-pyridine or a non-toxic, pharmacologically acceptable acid addition salt.

* * * * *